United States Patent [19]

Poirier

[11] 4,299,236
[45] Nov. 10, 1981

[54] INCENTIVE BREATHING EXERCISER

[75] Inventor: Victor L. Poirier, Chelmsford, Mass.

[73] Assignee: Thermo Electron Corporation, Waltham, Mass.

[21] Appl. No.: 87,288

[22] Filed: Oct. 22, 1979

[51] Int. Cl.³ .............................................. A61B 5/08
[52] U.S. Cl. .................................... 128/728; 272/99
[58] Field of Search .......... 128/728, 727, 725, 203.28, 128/204.28, 205.13–205.17; 272/99

[56] References Cited

U.S. PATENT DOCUMENTS

| | | | |
|---|---|---|---|
| 2,569,849 | 10/1951 | Emerson | 128/728 |
| 3,722,506 | 3/1973 | McMillan, Jr. | 128/727 |
| 3,754,546 | 8/1973 | Cooper | 128/727 |
| 3,769,967 | 11/1973 | Jones et al. | 128/728 X |
| 3,826,247 | 7/1974 | Ruskin et al. | 128/727 |
| 3,848,583 | 11/1974 | Parr | 128/728 |
| 4,025,070 | 5/1977 | McGill et al. | 128/727 X |
| 4,060,074 | 11/1977 | Russo | 128/727 |
| 4,096,855 | 6/1978 | Fleury, Jr. | 128/727 X |
| 4,114,608 | 9/1978 | Russo | 128/725 |

OTHER PUBLICATIONS

Gale et al., "The Bartlett-Edwards Incentive Spirometer: . . .", Canad. Anaesth. Soc. J., vol. 24, No. 3, May 1977.

Primary Examiner—Lee S. Cohen
Attorney, Agent, or Firm—Herbert E. Messenger; James L. Neal

[57] ABSTRACT

An inhalation device for use in respiratory therapy is described. The inhalation device or incentive breathing exerciser includes an inner bellows whose deflection allows accurate measurement of the initial volume of air inhaled by a patient and an outer bellows for measuring larger volumes of air after a valve in the inner bellows opens. The exerciser permits measurement of the true volume of air inhaled by a patient and is equipped with a simple timer for measuring the interval of time an inhaled breath is held. Removable handles and the flexible bellows permit collapse of the device for storage and shipment as a compact unit.

10 Claims, 4 Drawing Figures

INCENTIVE BREATHING EXERCISER

BACKGROUND OF THE INVENTION

This invention relates to an inhalation device or incentive breathing exerciser for use in respiratory therapy.

A recognized technique for treating patients with respiratory deficiencies or patients recovering from thoracic or abdominal surgery is the use of breathing exercisers. Such devices enable patients to strengthen and more fully utilize their respiratory systems, thus hastening recovery and avoiding complications such as pneumonia and lung collapse.

Among the inhalation devices presently known is that disclosed in U.S. Pat. No. 4,114,608. In using this device, a patient inhales through a tube connected near the bottom end of a container with a cylindrical wall and dome-shaped ends. Inhalation causes air to be drawn into the top end of the container through a port, then across the top end and into a larger port of a passageway leading down the wall to the breathing tube. The venturi effect associated with airflow between the ports causes a lightweight ball to rise from the bottom of the container, and continued inhalation keeps the ball suspended.

While the above-mentioned patent and references cited therein disclose a number of improvements in breathing exercisers such as reduced cost and complexity, the devices described cannot readily be used in certain types of respiratory therapy. In particular, since the prior art devices respond to inhalation rate, they are ill-suited for measuring the actual volume of air inhaled by a patient or for use in exercises wherein a patient takes a breath and holds the breath for a desired time interval. The holding of a deep breath for a measured time such as 2-4 seconds has been recognized as a valuable aspect of respiratory therapy.

Accordingly, it is an object of the invention to provide an inhalation device for accurately measuring the volume of air inspired by a patient.

It is another object of the invention to provide an incentive inhalation device for measuring the volume of air inspired by a patient and the length of time the inspired air is held by the patient.

It is also a object of the invention to provide an incentive inhalation device which, in addition to the foregoing, is compact, inexpensive, shatter-resistant, and easy to use.

SUMMARY OF THE INVENTION

The invention concerns a breathing exerciser comprising an inner bellows and a light-transmissive outer bellows from which air may be withdrawn by a patient. Both bellows have an upper end attached to a top member and a movable lower end whose deflection along a scale towards the top member permits measurement of the true volume inhaled by the patient.

In a preferred embodiment of the invention, the inhalation device includes handles connected between the top member and a base. The handles are easily removable and, with the handles removed, the flexible bellows collapse to permit storage and shipment of the inhalation device as a compact unit. To permit withdrawal of air from the device, one end of a flexible tube is connected to the base and an air passageway is formed between the inner bellows and the tube by hollow portions of the top member, of one of the handles, and of the base. As a patient inhales through a mouthpiece at the free end of the tube, air is withdrawn from within the inner bellows and its lower end deflects towards the top member. The true volume inhaled is determined by viewing the position of the lower end of the inner bellows relative to a scale. Actuating means such as plunger in the top member are provided to open a valve in the inner bellows as its lower end approaches the top member. This permits air to be withdrawn from the volume between the inner and outer bellows, and the resulting upward deflection of the lower end of the outer bellows permits continued measurement of the volume inhaled.

The inhalation device of the invention is particularly suited for a course of exercise wherein a patient takes a deep breath and holds the breath for an interval of time. To permit measurement of the time the breath is held, a simple timer may be provided in one handle of the device. No leak orifices or bleed holes are included in the device, and because of this the volume indicated by deflection of each bellows is the true volume inhaled. Also, the bellows remain in deflected position to record the inhaled volume for as long as the breath is held.

DETAILED DESCRIPTION OF PREFERRED EMBODIMENTS

Figure 1:
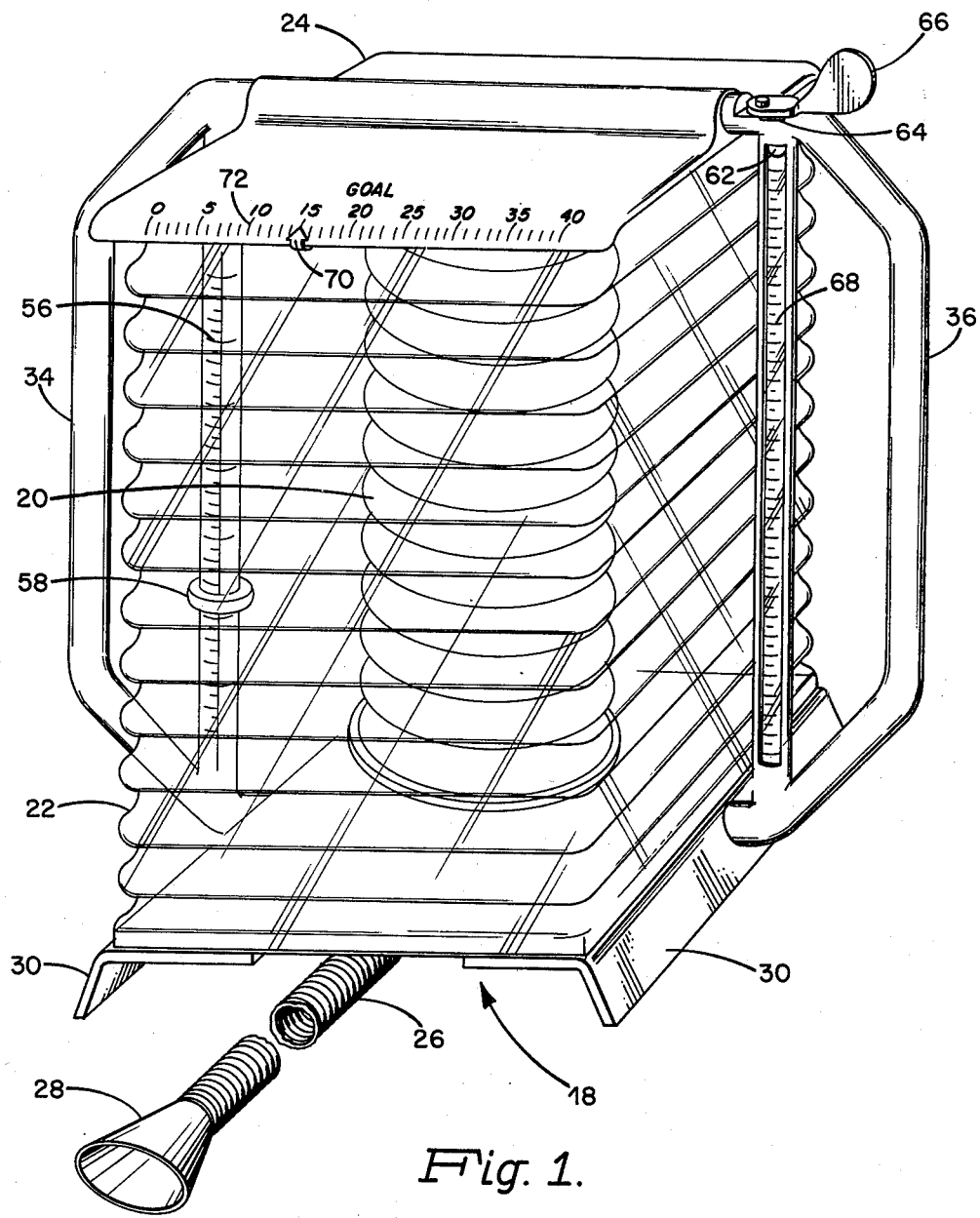
FIG. 1 is a perspective view of a preferred embodiment of the inhalation device of the invention.
Figure 2:
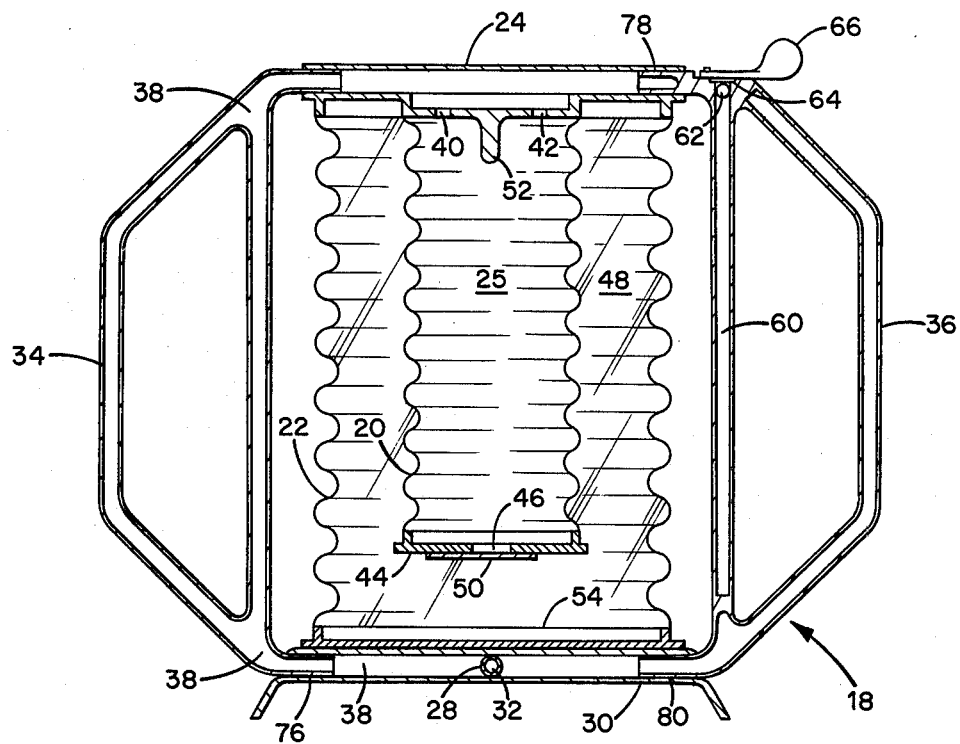
FIG. 2 is a cross-sectional side view of the inhalation device of FIG. 1 with the inner and outer bellows fully extended.
Figure 3:
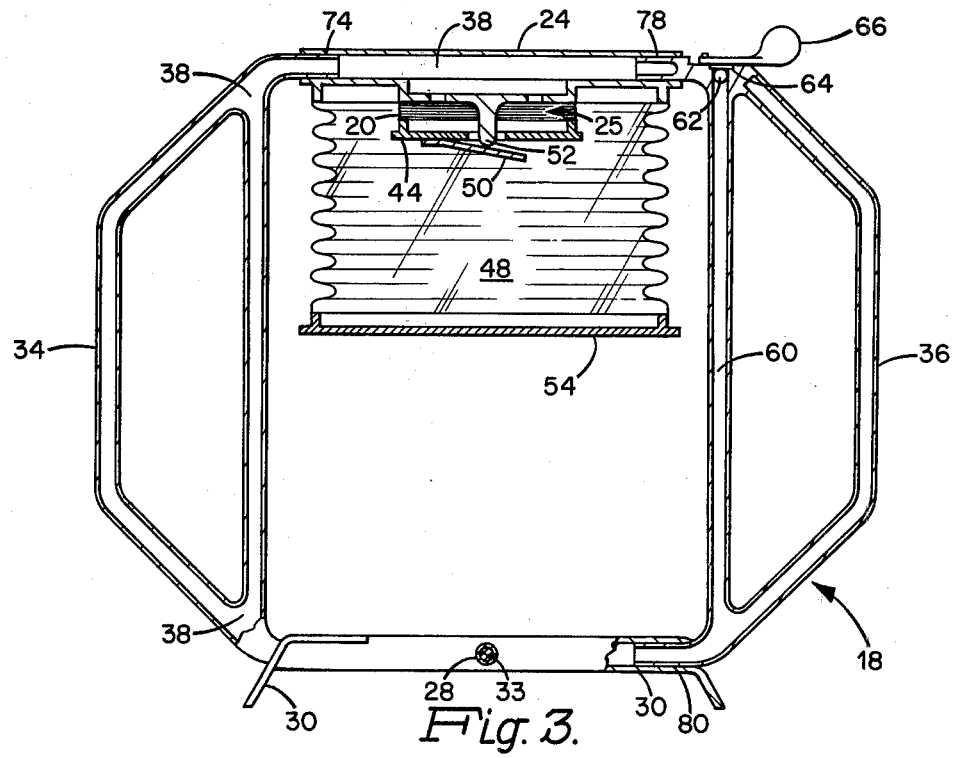
FIG. 3 is a cross-sectional view of the inhalation device during use showing the inner bellows in a retracted position.

As shown in FIGS. 1-3, a preferred inhalation device 18 according to the invention comprises an inner bellows 20 which is surrounded by an outer bellows 22. Each bellows has an upper end attached to a top member 24 and is collapsible from an extended position as shown in FIG. 1 to a retracted position such that the lower end of each bellows is adjacent to the top member 24 (FIG. 3 shows the inner bellows in retracted position and the outer bellows 22 in partially retracted position).

The inner bellows 20 and the top member 24 together define an inner chamber 25 with a comparatively low volume, e.g. 500 milliliters when the inner bellows 20 is in fully extended position. The inner bellows 20 is intended to measure the initial volume inhaled by a patient. It is particularly useful at the beginning of a patient's breathing therapy since large deflections of the lower end of the bellows 20 occur as the patient inhales, thus demonstrating a significant change for the patient's effort and providing an incentive to continue the therapy. Also, the large deflections facilitate accurate measurement of the volume of air withdrawn from the inner bellows 20 as discussed in more detail hereinafter.

To permit withdrawal of air from the inner bellows 20, the breathing exerciser 18 includes a flexible tube 26 with a mouthpiece 28 at one end thereof. The other end of the tube 26 is connected to a base 30 and communicates with a hollow portion of the base through a port 32. The tube preferably contains a porous filter 33 (FIG.

3) for preventing foreign material from entering the lungs of a patient.

For convenience in holding the inhalation device, and to provide communication between the tube 26 and the inner bellows 20, a pair of opposed handles 34 and 36 are attached to the base 30 and to the top member 24. An air passageway 38 is formed between the tube 26 and the interior of the inner bellows 20 by hollow portions of the top member 24, of the handle 34, and of the base 30. One or more ports in the top member 24 such as ports 40 and 42 shown in FIGS. 2 and 3 allow air to flow between the inner bellows 20 and the hollow portion of the top member 24 which forms part of the air passageway 38.

The inner bellows 20 has a port 46 in the lower end thereof to allow withdrawal of air from an outer chamber 48 defined by the outer bellows 22, the inner bellows 20, and the top member 24—i.e. the chamber 48 is the volume between the inner bellows 20 and the outer bellows 22. The inner bellows 20 may be a single, integral member or may include a stiffening plate 44 at its lower end (FIG. 2). A valve such as flapper valve 50 is attached to the stiffening plate 44 to block the port 46 during the initial inhalation of air from the breathing exerciser 18 and until the volume withdrawn is nearly equal to the total capacity of the inner bellows 20. As the lower end of the inner bellows moves upward in response to inhalation from the inner chamber 25 and reaches a position adjacent to the top member 24, valve actuating means such as a plunger 52 formed integrally with the top member 24 opens the valve 50 and allows air to be withdrawn from the volume between the inner bellows 20 and the outer bellows 22. Further inspiration by a patient produces upward movement of the lower end of the outer bellows 22, which, like inner bellows 20, may include a stiffening plate 54. A suitable capacity for the outer bellows 22 when fully extended is 3,000 milliliters.

To permit monitoring of the position of the inner bellows 20 during inspiration, the outer bellows 22 is fabricated from a transparent or other light-transmissive material and the inner bellows 20 preferably has a solid color so that it may be readily viewed through the outer bellows 22. The material for both bellows is selected to be light in weight and may, for example, be polyethylene of 3-4 mil. thickness. Since each bellows has a low weight, only a small amount of force is required during inhalation to move each bellows upwards towards the top member 24.

To allow measurement of the volume of air withdrawn from the exerciser 18, one or more scales are included in the device such as a scale 56 on the handle 34 (FIG. 1). The inspired volume, which is equal to the volume withdrawn from the exerciser 18, may be determined by reading the scale 56 at the point it is aligned with the lower end of the inner bellows 20, or with the lower end of the outer bellows 22 if the inspired volume exceeds the capacity of the inner chamber 25. Also, a slide ring 58 may be mounted on the handle 34 to record the volume achieved and to provide the patient with a visable goal for his next use of the device.

The scale 56 includes two sets of markings, one set for measuring the volume of air withdrawn from the outer bellows 22 and a second set for measuring the volume withdrawn from the inner bellows 20. As an alternative (not shown), the second set of markings may be included on the outer bellows 22 instead of on the handle 34. Either arrangement will allow simple, accurate determination of the volume of air withdrawn from the breathing exerciser 18.

One of the valuable respiratory exercises which can be performed with the inhalation device 18 of the present invention is the taking of a deep breath and holding that breath for a predetermined interval of time such as two to four seconds. To facilitate this form of therapy, the inner bellows 20 and the outer bellows 22 are substantially airtight with the exception of the ports 40 and 42 for withdrawal of air from the inner bellows 20 and the port 46 for withdrawal of air from the volume between the inner and outer bellows. That is, the bellows 20 and 22 have no leaks or bleed orifices which would require continued inhalation to maintain the contracted position of the bellows achieved by the patient. Also, the exerciser 18 includes a simple resettable timer for measuring the interval of time during which a patient holds his breath. In the preferred embodiment of the invention shown in FIGS. 1-3, the timer comprises a column of fluid 60 in a clear, hollow portion of handle 36 and an indicator such as a steel sphere 62 suspended in the fluid. The fluid is clear or translucent and has a viscosity selected such that the sphere will travel from top to bottom of the column 60 in a predetermined time such as four seconds. The sphere 62 is held near the top of the column 60 by a magnet 64 mounted on a swivel 66 external to the column. After the patient takes a deep breath and notes the volume achieved, he or she holds this breath and moves the swivel 66 to release the sphere. The sphere 62 falls through the fluid, and a scale 68 along the column 60 indicates the elapsed time after release of the sphere. To reset the timer, the swivel 66 is moved back and the exerciser 18 is inverted allowing the sphere to return to its initial position. The exerciser may then be repositioned upright for the next exercise.

If desired, the inhalation device 18 may include a goal counter such as an indicator 70 slidable along a scale 72 on the top member 24 to record the number of inhalations undertaken by the patient (see FIG. 1). A second slidable indicator (not shown) may be provided so that a patient can, for example, document his exercises for one day with the first indicator, leave this indicator at the number achieved, and then use the second indicator to document his attempts on the following day. This gives a patient a visable incentive to accomplish at least what he achieved on the previous day.

An important aspect of any inhalation device which is disposable and hence might be stored and used in large quantities (e.g. by hospitals) is the packaging and storage volume required. This volume is minimized for the device of the present invention since the breathing exerciser 18 is collapsible. The collapsibility is achieved in the preferred embodiments shown in FIGS. 1-3 by the use of the collapsible bellows 20 and 22 and the use of tapered hole and tube connections for attaching the handles 34 and 36 to the base 30 and top member 24 of the exerciser. For storage and shipment, the handles 34 and 36 may easily be removed from the holes 74, 76, 78, and 80 in the base 30 and top member 24, and the bellows 20 and 22 are then allowed to collapse. This disassembled exerciser 18 may then be stored or shipped in a package of considerably smaller height (e.g. by a factor of 3) than the height of the assembled unit. Reassembly for use requires only that the respiratory therapist insert the handles in the appropriate holes in the base 30 and the top member 24.

In use, the breathing exerciser 18 is either placed on a horizontal surface or held by the handles 34 and 36 in an approximately vertical position. The patient then closes his mouth about the mouthpiece 28 and inhales through the mouthpiece. This causes air to be drawn from within the inner bellows 20 through the ports 40 and 42 and into the portion of the air passageway 38 formed within the top member 24. The air flows successively through portions of the air passageway 38 in the top member 24, the handle 34, and the base 30 and then passes through the flexible tube 26 and into the patient's lungs. As air is withdrawn from the inner bellows 20, its lower end moves toward the top member 24 and the true volume of air inhaled may be accurately determined by the alignment of the lower end with the appropriate set of markings of the scale 56. When the volume of air inspired by the patient is sufficient to raise the lower end of the inner bellows 20 to a position adjacent to the top member 24, the plunger 52 contacts the flapper valve 50 and opens the valve. Air may then be withdrawn from the outer chamber 48 through the port 46 and again through the air passageway 38 to the patient's lungs. As this occurs, the lower end of the outer bellows 22 moves upward towards the top member 24 and the volume of air inspired may be determined by observing the alignment between the lower end of the outer bellows 22 and the scale 56. When the patient has finished inhaling, he holds his breath and activates the timer in the handle 36 by moving the swivel 66. This releases the magnetic sphere 62 to fall through the column of fluid 50, and the patient completes an exercise trial by successfully holding his breath for a time interval measured by travel of the sphere 62 along a prescribed portion of the column 60.

Figure 4:
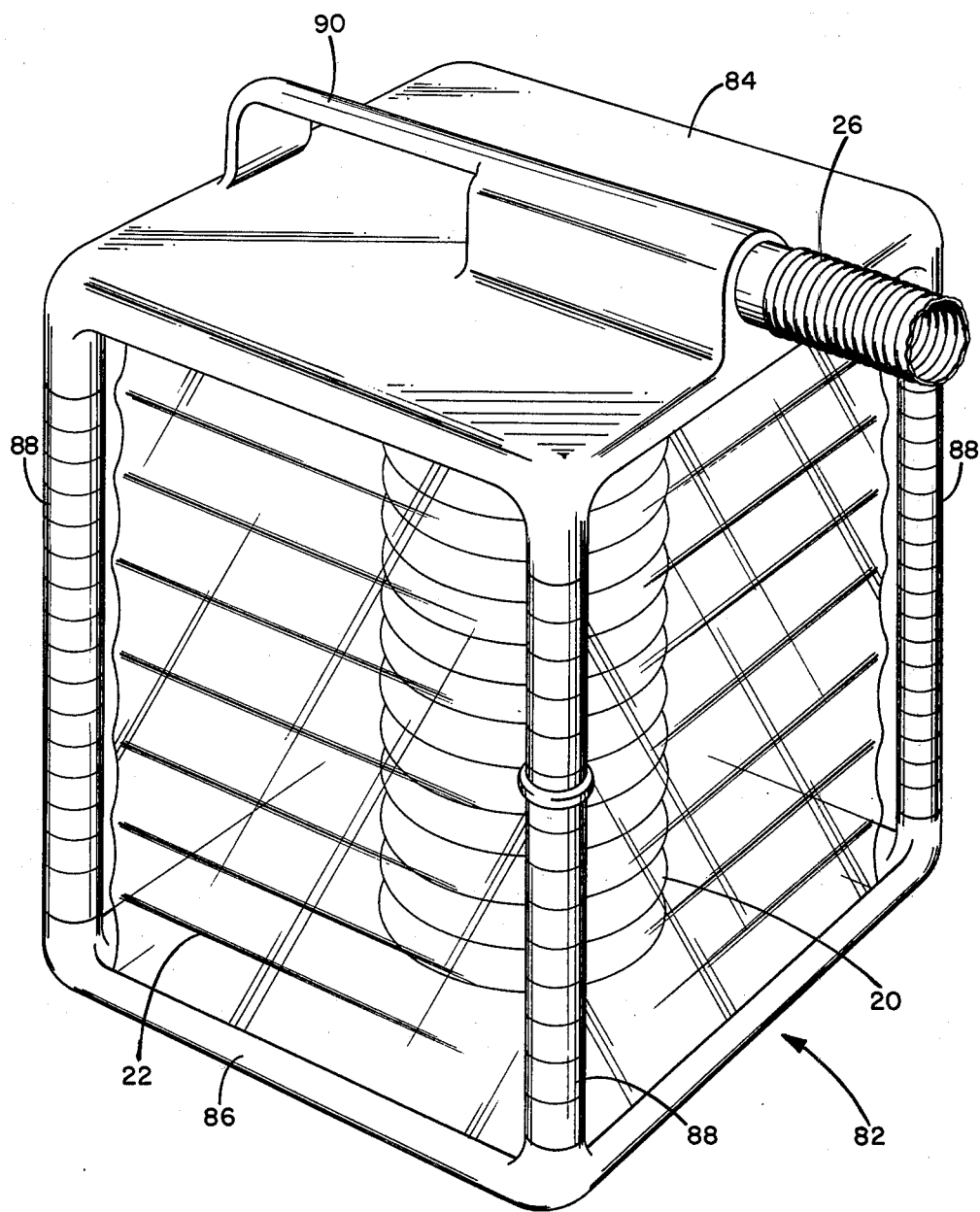
FIG. 4 is a perspective view of an alternate embodiment of the invention.

A slightly modified inhalation device 82 is shown in FIG. 4. This embodiment differs from the device 18 shown in FIGS. 1-3 in that the flexible tube 26 for withdrawal of air from the device 82 is connected to a top member 84 rather than to the base 86; the top member 84 in turn includes a hollow portion permitting airflow between the tube 26 and the inner bellows 20 of the device 82. Also, four removable legs or handles 88 are provided for connecting the top member 84 and the base 86. A handle or grip 90 may also be formed integrally with the top member 84.

While the invention has been shown and described with reference to preferred embodiments thereof, it is apparent that the inhalation device may be embodied in other specific forms without departing from the spirit or essential characteristics of the invention. The scope of the invention is indicated by the appended claims, and all changes which come within the meaning and range of equivalency of these claims are intended to be embraced therein.

What is claimed is:

1. An inhalation device comprising:
   a top member;
   an inner bellows including an upper end attached to said top member and a lower end movable towards said top member in response to the withdrawal of air from said inner bellows, said inner bellows having a port in said lower end;
   means for permitting a flow of air between the interior of said inner bellows and a location outside said inhalation device;
   a valve in the lower end of said inner bellows blocking said port during inhalation until the lower end of said inner bellows is moved to a position adjacent said top member;
   valve actuating means for opening said valve during inhalation as the lower end of said inner bellows is moved to a position adjacent said top member;
   an outer bellows spaced from an enclosing said inner bellows, said outer bellows including an upper end attached to said top member and a lower end movable towards said top member during inhalation as air is withdrawn from the volume between said inner and outer bellows; and
   means for measuring the volume of air withdrawn from said inner bellows and from the volume between said inner and outer bellows during inhalation.

2. An inhalation device as in claim 1 wherein said top member has a hollow portion and one or more ports providing fluid communication between said hollow portion and said inner bellows; and
   said means for permitting a flow of air between the interior of said inner bellows and a location outside said inhalation device includes a flexible inhalation tube attached to said top member and, when attached, being in fluid communication with said hollow portion of the top member.

3. An inhalation device is in claim 2 wherein said outer bellows is formed of a light transmissive material to permit observation of the position of said inner bellows.

4. An inhalation device as in claim 3 wherein said valve is a flapper valve and said valve actuating means comprises a plunger integral with said top member and extending into said inner bellows opposite said valve.

5. An inhalation device as in claim 1 wherein said top member has a hollow portion and one or more ports providing fluid communication between said hollow portion and said inner bellows, and said means for permitting a flow of air between the interior of said inner bellows and a location outside said inhalation device comprises:
   a base,
   a flexible inhalation tube attached to said base for permitting a patient to inhale air from said device; and
   at least one handle connected between said base and said top member;
   said handle and said base having hollow portions therein forming, together with the hollow portion of said top member, an inhalation passageway between said tube and said one or more ports in said top member.

6. An inhalation device as in claim 5 wherein said means for measuring the volume withdrawn from said inner bellows and from the volume between said inner and outer bellows comprises a scale on said handle.

7. An inhalation device as in claim 5 wherein said handle is one of a pair of opposed handles connected between said base and said top member and readily detachable therefrom to facilitate storage of said device in compact form, one of said handles including a timer for measuring the interval of time a patient holds air inhaled from said device.

8. An inhalation device as in claim 7 wherein said timer comprises:
   a sealed column of fluid;
   an indicator movable along said column through said fluid under the influence of gravity;
   means for holding said indicator at one end of said column and releasing it at a desired time for movement through said fluid; and a scale on said column for measuring the interval of elapsed time following release of said indicator.

9. An inhalation device as in claim 2 or claim 5 wherein said inner bellows, outer bellows, and top member together define an inner chamber and an outer chamber which are airtight except for permitting flow through said one or more ports in said top member and through said port in the lower end of said inner bellows.

10. An inhalation device comprising:

an inner bellows;

a top member having a hollow portion therein and one or more ports providing fluid communication between said hollow portion and said inner bellows;

an outer bellows spaced from and enclosing said inner bellows, said inner and outer bellows each having an upper end attached to said top member and a movable lower end;

said inner bellows having a port in the lower end thereof, said ports in said top member and said inner bellows providing the sole means for admitting air into and discharging air from said inner and outer bellows;

a flapper valve attached to said inner bellows blocking said port in the lower end of said inner bellows during inhalation until the lower end of said inner bellows is moved to a position adjacent to said top member;

a valve plunger integral with said top member and extending into said inner bellows opposite said valve for opening said valve as the lower end of said inner bellows is moved upward against said plunger;

a base;

a pair of opposed handles connected between said base and said top member; and a flexible inhalation tube attached to said base; said base, at least one of said handles, and said tube having hollow portions therein forming, together with the hollow portion of said top member, an inhalation passageway for permitting inhalation of air from said device through said one or more ports in said top member;

said device operable so that, upon inhalation, said inner bellows contracts with said valve closed from a fully expanded position in a direction towards said top member, and that, upon further inhalation, said flapper valve is opened by contact with said plunger and said outer bellows then contracts from a fully expanded position towards said top member.

* * * * *